US006387136B1

(12) United States Patent
Breton et al.

(10) Patent No.: US 6,387,136 B1
(45) Date of Patent: *May 14, 2002

(54) COMPOSITIONS FOR DYEING KERATIN FIBERS, CONTAINING 3-AMINOPYRAZOLINE DERIVATIVES AS COUPLER, DYEING PROCESS AND DYEING KIT

(75) Inventors: Philippe Breton, Le Chesnay; Alain Lagrange, Coupvray; Mireille Maubru, Chatou, all of (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/357,081

(22) Filed: Jul. 19, 1999

(30) Foreign Application Priority Data

Jul. 20, 1998 (FR) ............................................. 98 09224

(51) Int. Cl.$^7$ ................................................. A61K 7/13

(52) U.S. Cl. .................... 8/409; 8/407; 8/408; 8/410; 8/411; 8/412; 8/423

(58) Field of Search ............................ 8/407, 408, 409, 8/410, 411, 412, 423, 574

(56) References Cited

U.S. PATENT DOCUMENTS

| | | | | |
|---|---|---|---|---|
| 3,634,013 A | * | 1/1972 | Maul et al. ..................... 8/409 |
| 3,707,379 A | | 12/1972 | Haykawa et al. .............. 430/18 |
| 4,074,051 A | | 2/1978 | Stevens ....................... 544/140 |
| 4,149,005 A | * | 4/1979 | Battisti et al. ............... 548/362 |
| 4,268,436 A | * | 5/1981 | Pieri et al. ................... 260/141 |
| 4,347,251 A | | 8/1982 | Joseph et al. ................ 514/341 |
| 4,348,527 A | | 9/1982 | Dusza et al. ................. 548/362 |
| 4,360,680 A | | 11/1982 | Dusza et al. ................. 548/362 |
| 4,370,339 A | | 1/1983 | Haviv et al. ................. 514/404 |
| 4,432,991 A | | 2/1984 | Dusza et al. ................. 514/404 |
| 4,447,442 A | | 5/1984 | Dusza et al. ................. 514/404 |
| 4,448,783 A | | 5/1984 | Siegel ........................ 514/404 |
| 4,448,973 A | | 5/1984 | Dusza et al. ................. 548/362 |
| 4,451,479 A | | 5/1984 | Dusza et al. ................. 514/407 |
| 4,564,684 A | | 1/1986 | Copp et al. .................. 548/362 |
| 6,074,438 A | * | 6/2000 | Lim et al. ....................... 8/409 |
| 6,077,320 A | * | 6/2000 | Andrean et al. ................ 8/409 |

FOREIGN PATENT DOCUMENTS

| | | |
|---|---|---|
| CA | 2122509 | 9/1995 |
| DE | 19 24 721 | 12/1969 |
| DE | 2 008 693 | 9/1970 |
| DE | 23 59 399 | 6/1975 |
| DE | 2727706 | * 1/1978 |
| DE | 38 43 892 | 6/1990 |
| DE | 41 33 957 | 4/1993 |
| DE | 195 43 988 | 5/1997 |
| EP | 0 056 466 | 7/1982 |
| EP | 0 070 376 | 1/1983 |
| EP | 0 119 449 | 9/1984 |
| EP | 0 127 371 | 12/1984 |
| EP | 0 648 488 | 4/1995 |
| FR | 2 018 056 | 5/1970 |
| FR | 2 059 449 | 6/1971 |
| FR | 2 068 413 | 8/1971 |
| FR | 2 355 834 | 1/1978 |
| FR | 2 496 100 | 6/1982 |
| FR | 2 586 913 | 3/1987 |
| FR | 2 733 749 | 11/1996 |
| FR | 2 750 048 | 12/1997 |
| GB | 1 026 978 | 4/1966 |
| GB | 1 153 196 | 5/1969 |
| GB | 1 297 035 | 11/1972 |
| JP | 60-191254 | 9/1985 |
| JP | 3-223756 | 10/1991 |
| JP | 4-77471 | 3/1992 |
| JP | 7-110556 | 4/1995 |
| RO | 103091 | 9/1991 |
| WO | WO 90/14338 | 11/1990 |
| WO | WO 94/08969 | 4/1994 |
| WO | WO 94/08970 | 4/1994 |
| WO | WO 96/15765 | 5/1996 |

OTHER PUBLICATIONS

English language abstract of DD 2 93 958 (Abstract No. 116:46066), Sep. 1991.

English language abstract of SU 1227628 (Abstract No. 106:18539), Apr. 1986.

English language abstract of SU 194097 (Abstract No. 69:10434), Mar. 1967.

English language abstract of HU 2844 (Abstract No. 76:46201, Oct. 1971.

English language abstract of DD 228 663 (Abstract No. 105:143440), Oct. 1985.

CAPLUS Abstract of Credner, "Cyclization of an azomethine dye to a pyrazoloquinoxaline," Chem. Ber. 104(8), 1971.*

Zviak, The Science of Hair Care, Marcel Decker, NY, Chapter 8, pp. 263–286, 1986.*

J.–L. Barascut etal., "Étude de la tautomérie des aminopyrazolines. 1$^{re}$ partie: considérations générales et synthèse de produits à structure fixe. Tautomérie des amino–5pyrazolines.", Bull. Soc. Chim. Fr. 1970, 4, pp. 1571–1576.

(List continued on next page.)

Primary Examiner—Margaret Einsmann
(74) Attorney, Agent, or Firm—Finnegan, Henderson, Farabow, Garrett & Dunner, L.L.P.

(57) ABSTRACT

Novel compositions for the oxidation dyeing of keratin fibers, comprising at least one oxidation base and at least one specific 3-aminopyrazoline as coupler, and dyeing process and dyeing kit using this composition.

44 Claims, No Drawings

OTHER PUBLICATIONS

Fortuna Haviv et al., "3-[1-(2-Benzoxazolyl)hydrazino] propanenitrile Derivatives: Inhibitors of Immune Complex Induced Inflammation", J. Med. Chem 1988, pp. 1719–1728.

English language Derwent Abstract of DE 23 59 399, Jun. 1975.

English language Derwent Abstract of DE 38 43 892, Jun. 1990.

English language Derwent Abstract of DE 41 33 957, Apr. 1993.

English language Derwent Abstract of DE 195 43 988, May 1997.

English language Derwent Abstract of FR 2 018 056, May 1970.

English language Derwent Abstract of FR 2 355 834, Jan. 1978.

English language Derwent Abstract of FR 2 586 913, Mar. 1987.

English language Derwent Abstract of FR 2 733 749, Nov. 1996.

English language Derwent Abstract of FR 2 750 048, Dec. 1997.

English language Derwent Abstract of JP 2019576, Jan. 1990.

English language Derwent Abstract of DE 2 008 693, Sep. 1970.

English language Derwent Abstract of EP 0 648 488, Apr. 1995.

English language Derwent Abstract of FR 2 068 413, Aug. 1971.

English language Derwent Abstract of JP 60–191254, Sep. 1985.

English language Derwent Abstract of JP 3–223756, Oct. 1991.

English language Derwent Abstract of JP 4–77471, Mar. 1992.

English language Derwent Abstract of JP 7–110556, Apr. 1995.

English language Derwent Abstract of RO 103091, May 1992.

* cited by examiner

COMPOSITIONS FOR DYEING KERATIN FIBERS, CONTAINING 3-AMINOPYRAZOLINE DERIVATIVES AS COUPLER, DYEING PROCESS AND DYEING KIT

The invention relates to novel compositions for the oxidation dyeing of keratin fibers, comprising at least one oxidation base and at least one 3-aminopyrazoline derivative suitably selected as coupler, to the dyeing process using this composition and an oxidizing agent, as well as to the corresponding dyeing kit.

It is known practice to dye keratin fibers, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being chosen in particular from aromatic meta-diamines, meta-aminophenols, meta-diphenols and certain heterocyclic compounds.

The variety of compounds used with regards to the oxidation bases and the couplers can produce a wide range of colors.

The so-called "permanent" coloration obtained by means of these oxidation dyes preferably satisfies a certain number of requirements. Thus, it should have no toxicological drawbacks, it should be able to give shades of the desired intensity and it should be able to withstand external agents (light, bad weather, washing, permanent-waving, perspiration, rubbing).

The dyes should also be able to cover white hair and, lastly, they should be as unselective as possible, i.e. they should give the smallest possible color differences along the same length of keratin fiber, which may in fact be differently sensitized (i.e. damaged) between its tip and its root.

It has already been proposed, in particular in patent application FR-A-2,018,056, the disclosure of which is incorporated by reference herein, to use certain 3-aminopyrazolines as oxidation bases, i.e., more precisely, 1-(4'-aminophenyl)-3-aminopyrazolines or 1-(4'-hydroxyphenyl)-3-aminopyrazolines, for the oxidation dyeing of keratin fibers.

The inventors have discovered, entirely surprisingly and unexpectedly, that the use of certain 3-aminopyrazolines of formula (I) defined below, is not only suitable for use as couplers for oxidation dyeing, but that they can also give particularly intense colorations, especially when they are combined with heterocyclic oxidation bases. Moreover, they make it possible to obtain dye compositions giving colorations which show good resistance to the various attacking factors to which the hair may be subjected. Lastly, these compounds prove to be easily synthesized.

These discoveries form the basis of the present invention.

A first subject of the invention is thus a composition for the oxidation dyeing of keratin fibers, and in particular of human keratin fibers such as the hair, characterized in that it comprises, in a medium which is suitable for dyeing:
   at least one oxidation base, and
   at least one coupler chosen from 3-aminopyrazolines of formula (I) below and the acid addition salts thereof:

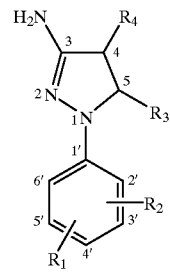

in which:
   $R_1$ and $R_2$, which may be identical or different, are chosen from a hydrogen atom; halogen atoms; $C_1-C_4$ alkyl radicals; $C_1-C_4$ monohydroxyalkyl radicals; $C_1-C_4$ polyhydroxyalkyl radicals; $(C_1-C_4)$alkoxy$(C_1-C_4)$alkyl radicals; radicals $OR_5$ in which $R_5$ is chosen from a hydrogen atom, $C_1-C_4$ alkyl radicals, aryl radicals, $C_1-C_4$ monohydroxyalkyl radicals, $C_2-C_4$ polyhydroxyalkyl radicals and $(C_1-C_4)$alkoxy$(C_1-C_4)$alkyl radicals;
   $R_3$ and $R_4$, which may be identical or different, are chosen from a hydrogen atom, halogen atoms; $C_1-C_4$ alkyl radicals; $C_1-C_4$ monohydroxyalkyl radicals; $C_2-C_4$ polyhydroxyalkyl radicals; $(C_1-C_4)$alkoxy$(C_1-C_4)$ alkyl radicals; $C_1-C_4$ aminoalkyl radicals; $C_1-C_4$ aminoalkyl radicals in which the amine is protected with a protecting group chosen from acetyl, amido, and sulphonyl radicals; $(C_1-C_4)$alkylamino$(C_1-C_4)$alkyl radicals; di[$(C_1-C_4)$alkyl]amino$(C_1-C_4)$alkyl radicals (it being possible for the dialkyls to form a 5- or 6-membered ring with the nitrogen atom to which they are bound, said ring being able to contain an additional heterocyclic atom); and mono[hydroxy$(C_1-C_4)$alkyl] amino$(C_1-C_4)$alkyl and di[hydroxy$(C_1-C_4)$alkyl] amino$(C_1-C_4)$alkyl radicals.

As mentioned above, the colorations obtained with the oxidation dye composition in accordance with the invention can be intense, most particularly when the compounds of formula (I) are used in combination with at least one heterocyclic oxidation base. The oxidation dye compositions in accordance with the invention furthermore make it possible to achieve shades in a very wide range of colors, which also can show excellent properties of resistance with respect to the action of the various external agents (light, bad weather, washing, permanent-waving, perspiration, rubbing).

In formula (I) above, the halogen atoms are chosen from bromine, chlorine, iodine and fluorine and the alkyl and alkoxy radicals can be linear or branched.

Among the 3-aminopyrazolines of formula (I) above which can be used as couplers in the dye compositions in accordance with the invention, mention may be made in particular of:
   3-amino-1-phenylpyrazoline,
   3-amino-1-phenyl-4-methylpyrazoline,
   3-amino-1-phenyl-5-methylpyrazoline,
   3-amino-1-phenyl-5-ethylpyrazoline,
   3-amino-1-phenyl-5-n-propylpyrazoline,
   3-amino-1-phenyl-5-isopropylpyrazoline,
   3-amino-1-(2'-bromophenyl)pyrazoline,
   3-amino-1-(3'-bromophenyl)pyrazoline,
   3-amino-1-(4'-bromophenyl)pyrazoline, 3-amino-1-(2'-chlorophenyl)pyrazoline,
3-amino-1-(2',4'-dichlorophenyl)pyrazoline,
3-amino-5-methyl-1-(2',4'-dichlorophenyl)-pyrazoline,
3-amino-1-(3'-chlorophenyl)pyrazoline,
3-amino-1-(2',5'-dichlorophenyl)pyrazoline,
3-amino-1-(2',6'-dichlorophenyl)pyrazoline,
3-amino-1-(3',4'-dichlorophenyl)pyrazoline,
3-amino-1-(3',4'-dichlorophenyl)-4-methyl-pyrazoline,
3-amino-1-(3',4'-dichlorophenyl)-5-methyl-pyrazoline,
3-amino-1-(3',4'-dichlorophenyl)-5-ethyl-pyrazoline,
3-amino-1-(3',5'-dichlorophenyl)pyrazoline,
3-amino-1-(3'-chloro-4'-methylphenyl)pyrazoline,
3-amino-5-methyl-1-(3'-chloro-4'-methylphenyl)-pyrazoline,
3-amino-1-(4'-amino-3'-chlorophenyl)pyrazoline,
3-amino-1-(4'-chlorophenyl)pyrazoline,
3-amino-1-(4'-chlorophenyl)-4-methylpyrazoline,
3-amino-1-(4'-chlorophenyl)-5-methylpyrazoline,
3-amino-1-(4'-chlorophenyl)-5-ethylpyrazoline,
3-amino-1-(4'-chlorophenyl)-5-n-propylpyrazoline,
3-amino-1-(4'-chlorophenyl)-4-n-butylpyrazoline,
3-amino-1-(4'-chlorophenyl)-5-n-butylpyrazoline,
3-amino-1-(2'-fluorophenyl)pyrazoline,
3-amino-1-(3'-fluorophenyl)pyrazoline,
3-amino-1-(4'-fluorophenyl)pyrazoline,
3-amino-1-(4'-fluorophenyl)-5-fluoropyrazoline,
3-amino-1-(4'-fluorophenyl)-4-methylpyrazoline,
3-amino-1-(4'-fluorophenyl)-5-methylpyrazoline,
3-amino-1-(4'-fluorophenyl)-5-ethylpyrazoline,
3-amino-1-(4'-fluorophenyl)-5-n-butylpyrazoline,
3-amino-5-methyl-1-(4'-fluorophenyl)pyrazoline,
3-amino-5-ethyl-1-(4'-fluorophenyl)pyrazoline,
3-amino-1-(4'-iodophenyl)pyrazoline,
3-amino-1-(2'-methylphenyl)pyrazoline,
3-amino-1-(3'-methylphenyl)pyrazoline,
3-amino-1-(4'-methylphenyl)pyrazoline,
3-amino-1-(4'-tert-butylphenyl)pyrazoline,
3-amino-1-(2'-methoxyphenyl)pyrazoline,
3-amino-1-(3'-methoxyphenyl)pyrazoline,
3-amino-1-(4'-methoxyphenyl)pyrazoline,
3-amino-1-(2'-ethoxyphenyl)pyrazoline,
3-amino-1-(3'-ethoxyphenyl)pyrazoline,
3-amino-1-(4'-ethoxyphenyl)pyrazoline,
3-amino-1-(4',3'-dimethoxyphenyl)pyrazoline, and the acid addition salts thereof.

Among these 3-aminopyrazolines of formula (I), the ones most particularly preferred are:
3-amino-1-phenylpyrazoline,
3-amino-1-(4'-fluorophenyl)pyrazoline,
3-amino-1-(4'-methoxyphenyl)pyrazoline, and the acid addition salts thereof.

The 3-aminopyrazoline derivative(s) of formula (I) in accordance with the invention and/or the acid addition salt(s) thereof preferably represent(s) from 0.0005 to 12% by weight approximately relative to the total weight of the dye composition and even more preferably from 0.005 to 6% by weight approximately relative to this weight.

The nature of the oxidation bases used in accordance with the invention is not critical. They can be chosen from the oxidation bases conventionally used in oxidation dyeing, and among which mention may be made in particular of para-phenylenediamines, double bases, para-aminophenols, ortho-aminophenols and heterocyclic bases.

Representative para-phenylenediamines include para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxy-ethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylene-diamine, 2-β-acetylaminoethyloxy-para-phenylenediamine and N-(β-methoxyethyl)-para-phenylenediamine, and the acid addition salts thereof.

Among the representative para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the acid addition salts thereof are most particularly preferred.

Representative double bases include N,N'-bis(β-hydroxyethyl)-N,Nβ-bis(4'-amino-phenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Representative para-aminophenols include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Representative ortho-aminophenols include 2-aminophenol, 2-amino-5-methylphenol, 2-amino-6-methylphenol and 5-acetamido-2-aminophenol, and the acid addition salts thereof.

Representative heterocyclic bases which can be used as oxidation bases in the dye compositions in accordance with the invention, include pyridines, pyrimidines and pyrazoles, and the acid addition salts thereof. The dye compositions containing a combination of a coupler of formula (I) and at least one heterocyclic oxidation base are particularly preferred according to the invention since they give particularly intense colorations.

Representative pyridines include the compounds described, for example, in patents GB 1,026,978 and GB 1,153,196, the disclosures of each which are specifically incorporated by reference herein, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Representative pyrimidines include the compounds described, for example, in German patent DE 2,359,399 or Japanese patent JP 88-169,571 or patent application WO 96/15765, the disclosures of each which are specifically incorporated by reference herein, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-tri-aminopyrimidine, and pyrazolopyrimidines such as those mentioned in patent application FR-A-2,750,048, the disclosure of which is specifically incorporated by reference herein, and among which mention may be made of pyrazolo[1,5-a]-pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidine-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl) (2-hydroxy-ethyl)amino]ethanol, 2-[(7-aminopyrazolo-[1,5-a]pyrimidin-3-yl) (2-hydroxyethyl) amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, and the addition salts thereof and tautomeric forms thereof, when a tautomeric equilibrium exists, and the acid addition salts thereof.

Representative pyrazoles include the compounds described in patents DE 3,843,892, DE 4,133,957 and patent applications WO 94/08969, WO 94/08970, FR-A-2,733,749 and DE 195 43 988, the disclosures of each of which are specifically incorporated by reference herein, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The oxidation base(s) preferably represent(s) from 0.0005 to 12% by weight approximately relative to the total weight of the dye composition and even more preferably from 0.005 to 6% by weight approximately relative to this weight.

In addition to the coupler(s) of formula (I) above, the dye composition in accordance with the invention can also contain one or more additional couplers which can be chosen from the couplers conventionally used in oxidation dyeing, and among which mention may be made in particular of meta-phenylenediamines, meta-aminophenols, meta-diphenols and heterocyclic couplers, such as, for example, indoles, indolines, pyridines and pyrazolones, and the acid addition salts thereof.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the acid addition salts thereof.

When they are present, the additional coupler(s) preferably represent from 0.0001 to 10% by weight approximately relative to the total weight of the dye composition, and even more preferably from 0.005 to 5% by weight approximately relative to this weight.

In general, the acid addition salts which can be used in the context of the dye compositions of the invention (compounds of formula (I), oxidation bases and additional couplers) are chosen in particular from the hydrochlorides, hydrobromides, sulphates, citrates, succinates, tartrates, lactates and acetates.

The medium which is suitable for dyeing (or the support) generally is water or a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably from 1 to 40% by weight approximately relative to the total weight of the dye composition, and even more preferably from 5 to 30% by weight approximately.

The pH of the dye composition in accordance with the invention generally ranges from 3 to 12 approximately and preferably from 5 to 11 approximately. It can be adjusted to the desired value using acidifying or basifying agents usually used for dyeing keratin fibers.

Among the acidifying agents which may be mentioned, by way of example, are inorganic or organic acids such as hydrochloric acid, orthophosphoric acid, sulphuric acid, carboxylic acids such as acetic acid, tartaric acid, citric acid and lactic acid, and sulphonic acids.

Representative basifying agents include aqueous ammonia, alkaline carbonates, alkanolamines such as mono-, di- and triethanolamine and derivatives thereof, sodium hydroxide, potassium hydroxide and the compounds of formula (II) below:

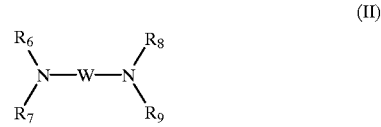

(II)

in which W is chosen from a propylene residue, optionally substituted with a hydroxyl group, and $C_1$–$C_6$ alkyl radicals; $R_6$, $R_7$, $R_8$ and $R_9$, which may be identical or different, are chosen from a hydrogen atom, $C_1$–$C_6$ alkyl radicals and $C_1$–$C_6$ hydroxyalkyl radicals.

The oxidation dye compositions in accordance with the invention can also contain at least one direct dye, in particular to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, fragrances, buffers, dispersing agents, conditioners such as, for example, volatile or non-volatile, modified or unmodified silicones, film-forming agents, ceramides, preserving agents, sunscreens and opacifiers.

Needless to say, a person skilled in the art will take care to select this or these optional complementary compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or any other form which is suitable for dyeing keratin fibers, and in particular human hair.

Another subject of the invention is the use of the 3-aminopyrazolines of formula (I) above and the acid addition salts thereof as couplers for the oxidation dyeing of keratin fibers, and in particular of human keratin fibers such as the hair.

Another subject of the invention is a process for the oxidation dyeing of keratin fibers, and in particular of human keratin fibers such as the hair, using the dye composition as defined above.

According to this process, at least one dye composition as defined above is applied to the fibers, the color being developed at acidic, neutral or alkaline pH using an oxidizing agent which is added to the dye composition only at the time of use, or which is present in an oxidizing composition which is applied simultaneously or sequentially.

According to one preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibers and is left to stand on them for preferably 3 to 50 minutes approximately, more preferably 5 to 30 minutes approximately, after which the fibers are rinsed, washed with shampoo, rinsed again and dried.

The oxidizing agent can be chosen from the oxidizing agents conventionally used for the oxidation dyeing of keratin fibers, and representative oxidizing agents include hydrogen peroxide, urea peroxide, alkali metal bromates, persalts such as perborates and persulphates, and enzymes such as peroxidases and 2-electron oxidoreductases. Hydrogen peroxide is particularly preferred.

The pH of the oxidizing composition containing the oxidizing agent as defined above is such that, after mixing with the dye composition, the pH of the resulting composition applied to the keratin fibers preferably ranges from 3 to 12 approximately, and even more preferably from 5 to 11. It is adjusted to the desired value using acidifying or basifying agents usually used for dyeing keratin fibers and as defined above.

The oxidizing composition as defined above can also contain various adjuvants conventionally used in compositions for dyeing the hair and as defined above.

The composition which is finally applied to the keratin fibers can be in various forms, such as in the form of liquids, creams or gels or in any other form which is suitable for dyeing keratin fibers, and in particular human hair.

Another subject of the invention is a multi-compartment dyeing device or dyeing "kit" or any other multi-compartment packaging system, a first compartment of which contains the dye composition as defined above and a second compartment of which contains the oxidizing composition as defined above. These devices can be equipped with a means for dispensing the desired mixture onto the hair, such as the devices described in patent FR-2,586,913, the disclosure of which is specifically incorporated by reference herein.

The 3-aminopyrazolines of formula (I) and acid addition salts thereof used as couplers in the dye compositions in accordance with the invention are known compounds which can be prepared, for example, according to a two-step process which is known in the literature and as described, for example, by F. Haviv et al., J. Med. Chem. 1988, 31, 1719–1728 and J-L. Barascut et al., Bull. Soc. Chim. Fr. 1970, 4, 1571–1576, the disclosures of each which are specifically incorporated by reference herein.

EXAMPLES

Examples 1 to 8 of Dyeing in Alkaline Medium

The dye compositions below, in accordance with the invention, were prepared (contents in grams):

| EXAMPLE | 1 | 2 | 3 | 4 | 5 | 6 | 7 | 8 |
|---|---|---|---|---|---|---|---|---|
| 3-Amino-1-(4'-fluorophenyl)pyrazoline monohydrochloride (coupler of formula (I)) | 0.647 | 0.647 | 0.647 | — | — | — | — | — |
| 3-Amino-1-phenylpyrazoline monohydrochloride (coupler of formula (I)) | — | — | — | 0.593 | 0.593 | 0.593 | — | — |
| 3-Amino-1-(4'-methoxyphenyl)pyrazoline monohydrochloride (coupler of formula (I)) | — | — | — | — | — | — | 0.683 | 0.683 |
| 4,5-Diamino-1,3-dimethylpyrazole dihydrochloride (oxidation base) | 0.597 | — | — | — | 0.597 | — | 0.597 | — |
| Pyrazolo[1,5-a]pyrimidine-3,7-diamine dihydrochloride (oxidation base) | — | 0.666 | — | — | — | 0.666 | — | 0.666 |

-continued

| EXAMPLE | 1 | 2 | 3 | 4 | 5 | 6 | 7 | 8 |
|---|---|---|---|---|---|---|---|---|
| para-Tolylenediamine (oxidation base) | — | — | 0.585 | 0.585 | — | — | — | — |
| Common dye support No. 1 | (*) | (*) | (*) | (*) | (*) | (*) | (*) | (*) |
| Demineralized water q. s. | 100 g | 100 g | 100 g | 100 g | 100 g | 100 g | 100 g | 100 g |

| Common dye support No. 1: | |
|---|---|
| 96° ethyl alcohol | 18 g |
| Sodium metabisulphite as an aqueous 35% solution | 0.68 g |
| Pentasodium salt of diethylenetriamino-pentaacetic acid | 1.1 g |
| Aqueous ammonia containing 20% $NH_3$ | 10 g |
| Demineralized water q.s. | 100 g |

| Common dye support No. 2: | |
|---|---|
| 96° ethanol | 18 g |
| Sodium metabisulphite as an aqueous 35% solution | 0.68 g |
| Pentasodium salt of diethylenetriamino-pentaacetic acid | 1.1 g |
| $K_2HPO_4/KH_2PO_4$ buffer (1.5M/1M) | 10 g |

Each dye composition was mixed, at the time of use, with an equal amount by weight of an oxidizing composition containing a 20-volumes hydrogen peroxide solution (6% by weight).

Each resulting composition had a pH in the region of 10±0.2 and was applied for 30 minutes to locks of natural grey hair containing 90% white hairs. The locks of hair were then rinsed, washed with a standard shampoo and then dried.

The locks of hair were dyed in the shades indicated in the table below:

| EXAMPLE | SHADE ON NATURAL HAIR |
|---|---|
| 1 | Slightly ash blue |
| 2 | Strong blue |
| 3 | Matt blond |
| 4 | Natural light blond |
| 5 | Ash light blond |
| 6 | Bluish light chestnut |
| 7 | Slightly green-blue very light blond |
| 8 | Slightly purplish blue |

Examples 9 to 17 of Dyeing in Neutral Medium

The dye compositions below, in accordance with the invention, were prepared (contents in grams):

Each dye composition above was mixed, at the time of use, with an equal amount by weight of an oxidizing composition consisting of a 20-volumes hydrogen peroxide solution (6% by weight).

Each resulting composition had a pH in the region of 6.8±0.2 and was applied for 30 minutes to locks of natural grey hair containing 90% white hairs. The locks of hair were then rinsed, washed with a standard shampoo and then dried.

The shades obtained are indicated in the table below:

| EXAMPLE | SHADE ON NATURAL HAIR |
|---|---|
| 9 | Turquoise |
| 10 | Blue |
| 11 | Irridescent ash-blond |
| 12 | Slightly green-blue |
| 13 | Blue |
| 14 | Ash natural blond |
| 15 | Slightly coppery matt golden blond |
| 16 | Green-blue |
| 17 | Ash-blue |

| EXAMPLE | 9 | 10 | 11 | 12 | 13 | 14 | 15 | 16 | 17 |
|---|---|---|---|---|---|---|---|---|---|
| 3-Amino-1-(4'-fluorophenyl)pyrazoline monohydrochloride (coupler of formula (I)) | 0.647 | 0.647 | — | — | — | — | — | — | — |
| 3-Amino-1-phenylpyrazoline monohydrochloride (coupler of formula (I)) | — | — | 0.593 | 0.593 | 0.593 | — | — | — | — |
| 3-Amino-1-(4'-methoxyphenyl)pyrazoline monohydrochloride (coupler of formula (I)) | — | — | — | — | — | 0.683 | 0.683 | 0.683 | 0.683 |
| 4,5-Diamino-1,3-dimethylpyrazole dihydrochloride (oxidation base) | 0.597 | — | — | 0.597 | — | — | 0.597 | — | — |
| Pyrazolo[1,5-a]pyrimidine-3,7-diamine dihydrochloride (oxidation base) | — | 0.666 | — | — | 0.666 | — | — | — | 0.666 |
| para-Tolylenediamine (oxidation base) | — | — | 0.585 | — | — | 0.585 | — | — | — |
| para-Aminophenol (oxidation base) | — | — | — | — | — | — | 0.327 | — | — |
| Common dye support No. 2 | () | () | ()g | () | () | () | () | () | (**) |
| Demineralized water q. s. | 100 g | 100 g | 100 g | 100 g | 100 g | 100 g | 100 g | 100 g | 100 g |

What is claimed is:

1. A composition for the oxidation dyeing of keratin fibers comprising:
   at least one oxidation base, and
   at least one coupler chosen from 3-amino-1-(4'-amino-3'-chlorophenyl)pyrazoline and 3-aminopyrazolines of formula (I) below and the acid addition salts thereof:

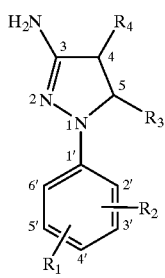

(I)

wherein:
$R_1$ and $R_2$, which may be identical or different, are each chosen from a hydrogen atom; halogen atoms; $C_1$–$C_4$ alkyl radicals; $C_1$–$C_4$ monohydroxyalkyl radicals; $C_1$–$C_4$ polyhydroxyalkyl radicals; $(C_1$–$C_4)$ alkoxy$(C_1$–$C_4)$alkyl radicals; and $OR_5$ radicals, wherein $R_5$ is chosen from $C_1$–$C_4$ alkyl radicals, aryl radicals, $C_1$–$C_4$ monohydroxyalkyl radicals, $C_2$–$C_4$ polyhydroxyalkyl radicals and $(C_1$–$C_4)$alkoxy $(C_1$–$C_4)$alkyl radicals;

$R_3$ and $R_4$, which may be identical or different, are each chosen from a hydrogen atom; halogen atoms; $C_1$–$C_4$ alkyl radicals; $C_1$–$C_4$ monohydroxyalkyl radicals; $C_2$–$C_4$ polyhydroxyalkyl radicals; $(C_1$–$C_4)$ alkoxy$(C_1$–$C_4)$alkyl radicals; $C_1$–$C_4$ aminoalkyl radicals; $(C_1$–$C_4)$alkylamino$(C_1$–$C_4)$alkyl radicals; di$((C_1$ –$C_4)$alkyl)amino$(C_1$–$C_4)$alkyl radicals wherein said dialkyls may optionally form a 5- or 6-membered ring with the nitrogen atom to which they are bound, said ring optionally containing a heterocyclic atom in addition to the nitrogen atom; mono(hydroxy$(C_1$–$C_4)$alkyl)amino$(C_1$–$C_4)$alkyl radicals and di(hydroxy$(C_1$–$C_4)$alkyl)amino$(C_1$–$C_4)$ alkyl radicals.

2. The composition according to claim 1, wherein said 3-aminopyrazolines of formula (I) are chosen from:
   3-amino-1-phenylpyrazoline,
   3-amino-1-phenyl-4-methylpyrazoline,
   3-amino-1-phenyl-5-methylpyrazoline,
   3-amino-1-phenyl-5-ethylpyrazoline,
   3-amino-1-phenyl-5-n-propylpyrazoline,
   3-amino-1-phenyl-5-isopropylpyrazoline,
   3-amino-1-(2'-bromophenyl)pyrazoline,
   3-amino-1-(3'-bromophenyl)pyrazoline,
   3-amino-1-(4'-bromophenyl)pyrazoline,
   3-amino-1-(2'-chlorophenyl)pyrazoline,
   3-amino-1-(2',4'-dichlorophenyl)pyrazoline,
   3-amino-5-methyl-1-(2',4-dichlorophenyl)-pyrazoline,
   3-amino-1-(3'-chlorophenyl)pyrazoline,
   3-amino-1-(2',5'-dichlorophenyl)pyrazoline,
   3-amino-1-(2',6'-dichlorophenyl)pyrazoline,
   3-amino-1-(3',4'-dichlorophenyl)pyrazoline,
   3-amino-1-(3',4'-dichlorophenyl)-4-methyl-pyrazoline,
   3-amino-1-(3',4'-dichlorophenyl)-5-methyl-pyrazoline,
   3-amino-1-(3',4'-dichlorophenyl)-5-ethyl-pyrazoline,
   3-amino-1-(3',5'-dichlorophenyl)pyrazoline,
   3-amino-1-(3'-chloro-4'-methylphenyl)pyrazoline,
   3-amino-5-methyl-1-(3'-chloro-4'-methylphenyl)-pyrazoline,
   3-amino-1-(4'-amino-3'-chlorophenyl)pyrazoline,
   3-amino-1-(4'-chlorophenyl)pyrazoline,
   3-amino-1-(4'-chlorophenyl)-4-methylpyrazoline,
   3-amino-1-(4'-chlorophenyl)-5-methylpyrazoline,
   3-amino-1-(4'-chlorophenyl)-5-ethylpyrazoline,
   3-amino-1-(4'-chlorophenyl)-5-n-propylpyrazoline,
   3-amino-1-(4'-chlorophenyl)-4-n-butylpyrazoline,
   3-amino-1-(4'-chlorophenyl)-5-n-butylpyrazoline,
   3-amino-1-(2'-fluorophenyl)pyrazoline,
   3-amino-1-(3'-fluorophenyl)pyrazoline,
   3-amino-1-(4'-fluorophenyl)pyrazoline,
   3-amino-1-(4'-fluorophenyl)-5-fluoropyrazoline,
   3-amino-1-(4'-fluorophenyl)-4-methylpyrazoline,
   3-amino-1-(4'-fluorophenyl)-5-methylpyrazoline,
   3-amino-1-(4'-fluorophenyl)-5-ethylpyrazoline,
   3-amino-1-(4'-fluorophenyl)-5-n-butylpyrazoline,
   3-amino-5-methyl-1-(4'-fluorophenyl)pyrazoline,
   3-amino-5-ethyl-1-(4'-fluorophenyl)pyrazoline,
   3-amino-1-(4'-iodophenyl)pyrazoline,
   3-amino-1-(2'-methylphenyl)pyrazoline,
   3-amino-1-(3'-methylphenyl)pyrazoline,
   3-amino-1-(4'-methylphenyl)pyrazoline,
   3-amino-1-(4'-tert-butylphenyl)pyrazoline,
   3-amino-1-(2'-methoxyphenyl)pyrazoline,
   3-amino-1-(3'-methoxyphenyl)pyrazoline,
   3-amino-1-(4'-methoxyphenyl)pyrazoline,
   3-amino-1-(2'-ethoxyphenyl)pyrazoline,
   3-amino-1-(3'-ethoxyphenyl)pyrazoline,
   3-amino-1-(4'-ethoxyphenyl)pyrazoline,
   3-amino-1-(4',3'-dimethoxyphenyl)pyrazoline, and the acid addition salts thereof.

3. The composition according to claim 2, wherein said 3-aminopyrazolines of formula (I) are chosen from:
   3-amino-1-phenylpyrazoline,
   3-amino-1-(4'-fluorophenyl)pyrazoline,
   3-amino-1-(4'-methoxyphenyl)pyrazoline, and the acid addition salts thereof.

4. The composition according to claim 1, wherein said keratin fibers are human keratin fibers.

5. The composition according to claim 4, wherein said human keratin fibers are hair.

6. The composition according to claim 1, wherein said halogen atoms are chosen from bromine, chlorine, iodine, and fluorine.

7. The composition according to claim 1, wherein said at least one oxidation base and said at least one coupler are present in said composition in an amount sufficient for oxidation dyeing.

8. The composition according to claim 1, wherein the amino of said $C_1$–$C_4$ amino alkyl radicals are protected by radicals chosen from an acetyl radical, amido radicals, and sulphonyl radicals.

9. The composition according to claim 1, wherein said at least one coupler is present in an amount ranging from 0.0005 to 12% by weight relative to the total weight of the dye composition.

10. The composition according to claim 9, wherein said at least one coupler is present in an amount ranging from 0.005 to 6% by weight relative to the total weight of the dye composition.

11. The composition according to claim 1, wherein said at least one oxidation base is chosen from para-phenylenediamines, double bases, para-aminophenols, ortho-aminophenols and heterocyclic bases.

12. The composition according to claim 1, wherein said at least one oxidation base is chosen from heterocyclic bases.

13. The composition according to claim 11, wherein said para-phenylenediamines are chosen from para-phenylenediamine, para-tolylene-diamine, 2-chloro-para-phenylenediamine, 2,3-dimethyl-para-phenylenediamine, 2,6-dimethyl-para-phenylene-diamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxy-ethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

14. The composition according to claim 11, wherein said double bases are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diaminophenoxy)-3,5-dioxaoctane, and the acid addition salts thereof.

15. The composition according to claim 11, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

16. The composition according to claim 11, wherein said ortho-aminophenols are chosen from 2-aminophenol, 2-amino-5-methylphenol, 2-amino-6-methylphenol and 5-acetamido-2-aminophenol, and the acid addition salts thereof.

17. The composition according to claim 11, wherein said heterocyclic bases are chosen from pyridines, pyrimidines, pyrazoles and pyrazolopyrimidines, and the acid addition salts thereof.

18. The composition according to claim 17, wherein said pyridines are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

19. The composition according to claim 17, wherein said pyrimidines are chosen from 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine.

20. The composition according to claim 17, wherein said pyrazolopyrimidines are chosen from pyrazolo[1,5-a]-pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidine-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl) (2-hydroxy-ethyl)amino]ethanol, 2-[(7-aminopyrazolo-[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, and the acid addition salts thereof and tautomeric forms thereof, when a tautomeric equilibrium exists, and the acid addition salts of said tautomeric forms.

21. The composition according to claim 17, wherein said pyrazoles are chosen from 4,5-diamino-1-methylpyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-($\mu$-3-hydroxyethyl)amino-1-methylpyrazole, and the acid addition salts thereof.

22. The composition according to claim 1, wherein said at least one oxidation base is present in an amount ranging from 0.0005 to 12% by weight relative to the total weight of the dye composition.

23. The composition according to claim 22, wherein said at least one oxidation base is present in an amount ranging from 0.005 to 6% by weight relative to the total weight of the dye composition.

24. The composition according to claim 1, wherein said composition further comprises at least one additional coupler chosen from meta-phenylenediamines, meta-aminophenols, meta-diphenols and heterocyclic couplers, and the addition salts thereof with an acid.

25. The composition according to claim 24, wherein said heterocyclic couplers are chosen from indoles, indolines, pyridines, and pyrazolones.

26. The composition according to claim 24, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, and 1-phenyl-3-methylpyrazol-5-one, and the acid addition salts thereof.

27. The composition according to claim 24, wherein said at least one additional coupler is present in an amount ranging from 0.0001 to 10% by weight relative to the total weight of the dye composition.

28. The composition according to claim 24, wherein said at least one additional coupler is present in an amount ranging from 0.0005 to 5% by weight relative to the total weight of the dye composition.

29. The composition according to claim 24, wherein said acid addition salts are chosen from hydrochlorides, hydrobromides, sulphates, citrates, succinates, tartrates, lactates and acetates.

30. The composition according to claim 1, wherein said composition further comprises a medium chosen from water or a mixture of water and at least one organic solvent.

31. The composition according to claim 1, wherein said composition has a pH ranging from 3 to 12.

32. The composition according to claim 31, wherein said composition has a pH ranging from 5 to 11.

33. The composition according to claim 1, wherein said composition further comprises at least one direct dye.

34. The composition according claim 1, wherein said composition is in a form chosen from a liquid, a cream, and a gel.

35. The composition according to claim 1, wherein said composition further comprises an oxidizing agent.

36. The composition according to claim 35, wherein said oxidizing agent is chosen from hydrogen peroxide, urea peroxide, alkali metal bromates, persalts and enzymes.

37. The composition according to claim 36, wherein said persalts are chosen from perborates and persulphates.

38. The composition according to claim 36, wherein said enzymes are chosen from peroxidases and 2-electron oxidoreductases.

39. A process for dyeing keratin fibers, comprising
separately storing a first composition,
separately storing a second composition,
thereafter mixing said first and second compositions,
applying said mixture to said fibers, and
developing for a period of time sufficient to achieve a desired coloration,
wherein said first composition comprises
at least one oxidation base, and
at least one coupler chosen from 3-aminopyrazolines of formula (I) below and the acid addition salts thereof:

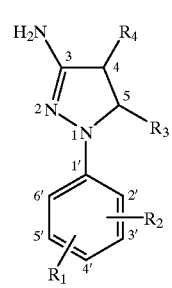

(I)

in which:

$R_1$ and $R_2$, which may be identical or different, are chosen from a hydrogen atom; halogen atoms; $C_1$–$C_4$ alkyl radicals; $C_1$–$C_4$ monohydroxyalkyl radials; $C_1$–$C_4$ polyhydroxyalkyl radicals; $(C_1$–$C_4)$alkoxy$(C_1$–$C_4)$alkyl radicals; and $OR_5$ radicals, in which $R_5$ is chosen from $C_1$–$C_4$ alkyl radicals, aryl radicals, $C_1$–$C_4$ monohydroxyalkyl radicals, $C_2$–$C_4$ polyhydroxyalkyl radicals and $(C_1$–$C_4)$ alkoxy$(C_1$–$C_4)$alkyl radicals;

$R_3$ and $R_4$, which may be identical or different, are chosen from a hydrogen atom; halogen atoms; $C_1$–$C_4$ alkyl radicals; $C_1$–$C_4$ monohydroxyalkyl radicals; $C_2$–$C_4$ polyhydroxyalkyl radicals; $(C_1$–$C_4)$alkoxy$(C_1$–$C_4)$alkyl radicals; $C_1$–$C_4$ aminoalkyl radicals; $(C_1$–$C_4)$alkylamino$(C_1$–$C_4)$alkyl radicals; di[$(C_1$–$C_4)$alkyl]amino$(C_1$–$C_4)$alkyl radicals; mono[hydroxy$(C_1$–$C_4)$alkyl]amino $(C_1$–$C_4)$alkyl radicals and di[hydroxy$(C_1$–$C_4)$ alkyl]amino$(C_1$–$C_4)$alkyl radicals and wherein said second composition comprises an oxidizing agent.

40. A process for dyeing keratin fibers, comprising applying a composition for the oxidation dyeing of keratin fibers to said keratin fibers and developing for a period of time sufficient to achieve a desired coloration, wherein said composition comprises:

at least one oxidation base, and at least one coupler chosen from 3-aminopyrazolines of formula (I) below and the acid addition salts thereof:

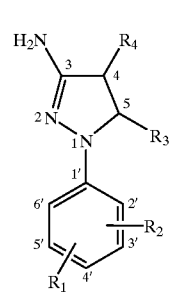

(I)

in which:

$R_1$ and $R_2$, which may be identical or different, are chosen from a hydrogen atom; halogen atoms;

$C_1$–$C_4$ alkyl radicals; $C_1$–$C_4$ monohydroxyalkyl radials; $C_1$–$C_4$ polyhydroxyalkyl radicals; ($C_1$–$C_4$) alkoxy($C_1$–$C_4$)alkyl radicals; and $OR_5$ radicals, in which $R_5$ is chosen from $C_1$–$C_4$ alkyl radicals, aryl radicals, $C_1$–$C_4$ monohydroxyalkyl radicals, $C_2$–$C_4$ polyhydroxyalkyl radicals and ($C_1$–$C_4$)alkoxy ($C_1$–$C_4$)alkyl radicals;

$R_3$ and $R_4$, which may be identical or different, are chosen from a hydrogen atom; halogen atoms; $C_1$–$C_4$ alkyl radicals; $C_1$–$C_4$ monohydroxyalkyl radicals; $C_2$–$C_4$ polyhydroxyalkyl radicals; ($C_1$–$C_4$) alkoxy($C_1$–$C_4$)alkyl radicals; $C_1$–$C_4$ aminoalkyl radicals; ($C_1$–$C_4$)alkylamino($C_1$–$C_4$)alkyl radicals; di[($C_1$–$C_4$)alkyl]amino($C_1$–$C_4$)alkyl radicals; mono[hydroxy($C_1$–$C_4$)alkyl]amino($C_1$–$C_4$)alkyl radicals and di[hydroxy($C_1$–$C_4$)alkyl]amino($C_1$–$C_4$)alkyl radicals.

41. The process according to claim 40, further comprising rinsing said keratin fibers, washing said keratin fibers with shampoo, a second rinsing of said keratin fibers and drying of said keratin fibers.

42. A multi-compartment dyeing kit, comprising at least two separate compartments, wherein a first compartment contains a first composition and a second compartment contains a second composition, wherein said first composition comprises at least one oxidation base, and at least one coupler chosen from 3-aminopyrazolines of formula (I) below and the acid addition salts thereof:

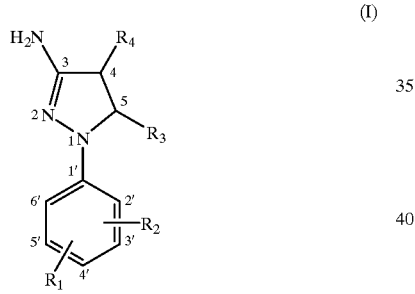

(I)

in which:

$R_1$ and $R_2$, which may be identical or different, are chosen from a hydrogen atom; halogen atoms; $C_1$–$C_4$ alkyl radicals; $C_1$–$C_4$ monohydroxyalkyl radials; $C_1$–$C_4$ polyhydroxyalkyl radicals; ($C_1$–$C_4$)alkoxy($C_1$–$C_4$)alkyl radicals; and $OR_5$ radicals, in which $R_5$ is chosen from $C_1$–$C_4$ alkyl radicals, aryl radicals, $C_1$–$C_4$ monohydroxyalkyl radicals, $C_2$–$C_4$ polyhydroxyalkyl radicals and ($C_1$–$C_4$) alkoxy($C_1$–$C_4$)alkyl radicals;

$R_3$ and $R_4$, which may be identical or different, are chosen from a hydrogen atom; halogen atoms; $C_1$–$C_4$ alkyl radicals; $C_1$–$C_4$ monohydroxyalkyl radicals; $C_2$–$C_4$ polyhydroxyalkyl radicals; ($C_1$–$C_4$)alkoxy($C_1$–$C_4$)alkyl radicals; $C_1$–$C_4$ aminoalkyl radicals; ($C_1$–$C_4$)alkylamino($C_1$–$C_4$)alkyl radicals; di[($C_1$–$C_4$)alkyl]amino($C_1$–$C_4$)alkyl radicals; mono[hydroxy($C_1$–$C_4$)alkyl]amino ($C_1$–$C_4$)alkyl radicals and di[hydroxy($C_1$–$C_4$) alkyl]amino($C_1$–$C_4$)alkyl radicals and wherein said second composition comprises an oxidizing composition.

43. A process for dyeing keratin fibers, comprising separately storing a first composition, separately storing a second composition, thereafter mixing said first and second compositions, applying said mixture to said fibers, and developing for a period of time sufficient to achieve a desired coloration, wherein said first composition comprises at least one oxidation base, and at least one coupler chosen from 3-amino-1-(4'-amino-3'-chlorophenyl)pyrazoline and 3-aminopyrazolines of formula (I) below and the acid addition salts thereof:

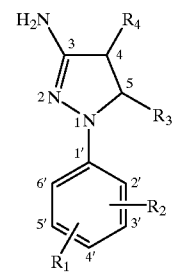

(I)

in which:

$R_1$ and $R_2$, which may be identical or different, are chosen from a hydrogen atom; halogen atoms; $C_1$–$C_4$ alkyl radicals; $C_1$–$C_4$ monohydroxyalkyl radials; $C_1$–$C_4$ polyhydroxyalkyl radicals; ($C_1$–$C_4$)alkoxy($C_1$–$C_4$)alkyl radicals; and $OR_5$ radicals, in which $R_5$ is chosen from $C_1$–$C_4$ alkyl radicals, aryl radicals, $C_1$–$C_4$ monohydroxyalkyl radicals, $C_2$–$C_4$ polyhydroxyalkyl radicals and ($C_1$–$C_4$) alkoxy($C_1$–$C_4$)alkyl radicals;

$R_3$ and $R_4$, which may be identical or different, are chosen from a hydrogen atom; halogen atoms; $C_1$–$C_4$ alkyl radicals; $C_1$–$C_4$ monohydroxyalkyl radicals; $C_2$–$C_4$ polyhydroxyalkyl radicals; ($C_1$–$C_4$)alkoxy($C_1$–$C_4$)alkyl radicals; $C_1$–$C_4$ aminoalkyl radicals; ($C_1$–$C_4$)alkylamino($C_1$–$C_4$)alkyl radicals; di[($C_1$–$C_4$)alkyl]amino($C_1$–$C_4$)alkyl radicals; mono[hydroxy($C_1$–$C_4$)alkyl]amino ($C_1$–$C_4$)alkyl radicals and di[hydroxy($C_1$–$C_4$) alkyl]amino($C_1$–$C_4$)alkyl radicals and wherein said second composition comprises an oxidizing composition containing at least one oxidizing agent.

44. A process for dyeing keratin fibers comprising, separately storing a first composition, separately storing a second composition, then sequentially applying said first composition and second compositions to said keratin fibers, and developing for a period of time sufficient to achieve a desired coloration, wherein said first composition comprises at least one oxidation base, and at least one coupler chosen from 3-amino-1-(4'-amino-3'-chlorophenyl)pyrazoline and 3-aminopyrazolines of formula (I) below and the acid addition salts thereof:

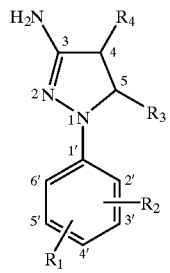 (I)

in which:

R$_1$ and R$_2$, which may be identical or different, are chosen from a hydrogen atom; halogen atoms; C$_1$–C$_4$ alkyl radicals; C$_1$–C$_4$ monohydroxyalkyl radicals; C$_1$–C$_4$ polyhydroxyalkyl radicals; (C$_1$–C$_4$)alkoxy(C$_1$–C$_4$)alkyl radicals; and OR$_5$ radicals, in which R$_5$ is chosen from C$_1$–C$_4$ alkyl radicals, aryl radicals, C$_1$–C$_4$ monohydroxyalkyl radicals, C$_2$–C$_4$ polyhydroxyalkyl radicals and (C$_1$–C$_4$)alkoxy(C$_1$–C$_4$)alkyl radicals;

R$_3$ and R$_4$, which may be identical or different, are chosen from a hydrogen atom; halogen atoms; C$_1$–C$_4$ alkyl radicals; C$_1$–C$_4$ monohydroxyalkyl radicals; C$_2$–C$_4$ polyhydroxyalkyl radicals; (C$_1$–C$_4$)alkoxy(C$_1$–C$_4$)alkyl radicals; C$_1$–C$_4$ aminoalkyl radicals; (C$_1$–C$_4$)alkylamino(C$_1$–C$_4$)alkyl radicals; di[(C$_1$–C$_4$)alkyl]amino(C$_1$–C$_4$)alkyl radicals; mono[hydroxy(C$_1$–C$_4$)alkyl]amino (C$_1$–C$_4$)alkyl radicals and di[hydroxy(C$_1$–C$_4$)alkyl]amino(C$_1$–C$_4$)alkyl radicals and wherein said second composition comprises an oxidizing composition, wherein said oxidizing composition comprises at least one oxidizing agent.

* * * * *

UNITED STATES PATENT AND TRADEMARK OFFICE
CERTIFICATE OF CORRECTION

PATENT NO.    : 6,387,136 B1
DATED         : May 14, 2002
INVENTOR(S)   : Philippe Breton et al.

It is certified that error appears in the above-identified patent and that said Letters Patent is hereby corrected as shown below:

Column 11,
Line 38, "$((C_1 -C_4)alkyl)$" should read -- $((C_1-C_4)alkyl)$ --.

Column 14,
Lines 51 and 52, "$(\mu\text{-3-hydroxyethyl})$" should read -- $(\beta\text{-hydroxyethyl})$ --.

Column 17,
Line 2, "radials" should read -- radicals --.

Column 18,
Line 58, after "said first", delete "composition".

Signed and Sealed this

Sixth Day of August, 2002

Attest:

Attesting Officer

JAMES E. ROGAN
Director of the United States Patent and Trademark Office